United States Patent [19]

Takase et al.

[11] Patent Number: 4,804,668
[45] Date of Patent: Feb. 14, 1989

[54] THIAZOLE DERIVATIVES AND MEDICAL COMPOSITIONS THEREOF

[75] Inventors: Muneaki Takase; Kimitomo Yoshioka, both of Tokyo; Hiroaki Yamazaki, Ibaragi, all of Japan

[73] Assignee: Zenyaku Kogyo Kabushiki Kaisha, Tokyo, Japan

[21] Appl. No.: 844,615

[22] Filed: Mar. 27, 1986

[30] Foreign Application Priority Data

Mar. 27, 1985 [JP] Japan ................. 60-62575

[51] Int. Cl.$^4$ ............... C07D 417/04; A61K 31/38; A61K 31/425
[52] U.S. Cl. ..................... 514/314; 546/167; 546/284; 548/146; 514/338; 514/365
[58] Field of Search ............ 546/284, 167; 548/146; 514/317, 338, 365

[56] References Cited

U.S. PATENT DOCUMENTS

| | | | |
|---|---|---|---|
| 4,320,125 | 3/1982 | Puttner et al. | 548/205 X |
| 4,612,321 | 9/1986 | Terao et al. | 546/280 |
| 4,623,377 | 11/1986 | Kurahashi et al. | 546/165 |
| 4,649,146 | 3/1987 | Takaya et al. | 514/307 |

*Primary Examiner*—David B. Springer
*Attorney, Agent, or Firm*—Scrivener and Clarke

[57] ABSTRACT

A thiazole derivative represented by the formula I, pharmaceutically acceptable acid addition salt thereof, and a process for preparation thereof

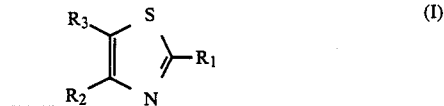 (I)

wherein
$R_1$ represents —COOR$_4$,

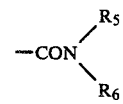

or cyano wherein
$R_4$ represents hydrogen or lower alkyl, and
$R_5$ and $R_6$ may be the same or different and represent hydrogen, lower alkyl, aryl, amino-lower alkyl, N-lower alkylamino-lower alkyl, N,N-di-lower alkylamino-lower alkyl or $R_5$ and $R_6$ are joined to form a N-containing heterocyclic group;
$R_2$ represents hydrogen or lower alkyl; and
$R_3$ represents N-containing heterocyclic group.

These compounds are useful as cardiotonic agents.

28 Claims, No Drawings

THIAZOLE DERIVATIVES AND MEDICAL COMPOSITIONS THEREOF

BACKGROUND OF THE INVENTION

The present invention relates to a thiazole derivative represented by the formula I, pharmaceutically acceptable acid addition salt thereof, and a process for preparation thereof

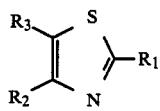

wherein
$R_1$ represents —COOR$_4$,

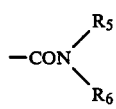

or cyano wherein
$R_4$ represents hydrogen or lower alkyl, and
$R_5$ and $R_6$ may be same or different and represent hydrogen, lower alkyl, aryl, amino-lower alkyl, N-lower alkylamino-lower alkyl, N,N-di-lower alkylamino-lower alkyl or $R_5$ and $R_6$ are joined to form N-containing heterocyclic group;
$R_2$ represents hydrogen or lower alkyl; and
$R_3$ represents N-containing heterocyclic group.

Some thiazole derivatives having a cardiotonic activity are known as described in Japanese Patent Applications laid open under Nos. 134417/1982, 16889/1984 and 193878/1984 and so on. Meanwhile, thiazole derivatives in general are prepared by a method as described in Japanese Patent Applications laid open under Nos. 34241/1982, 49969/1974 and so on. That is, a thioamide is reacted with an α-halocarbonyl compound to form a compound of thiazole derivative. The known thiazole derivatives having a cardiotonic activity is prepared by this well known method.

However, there is no teaching in the prior art of any cardiotonically active compounds having any chemical structure comparable to or suggestive of instantly claimed compound.

Further, such known technique is unsuitable for synthesizing the compound of the formula I.

SUMMARY OF THE INVENTION

As the result of researches, we, the inventors succeeded in synthesizing new thiazole derivatives which are useful as cardiotonic agents. More specifically, one aspect of this invention is to provide thiazole derivatives having carbonyl, unsubstituted or substituted aminocarbonyl or cyano at position 2 and having nitrogen-containing heterocyclic group at position 5 and and pharmaceutically acceptable acid addition salt thereof. Another aspect of this invention is to provide a cardiotonic agent comprising said thiazole derivatives and pharmaceutically acceptable acid addition salt thereof as effective component. A further aspect of this invention is to provide a process for preparation of said thiazole derivatives and pharmaceutically acceptable acid addition salt thereof.

DETAILED DESCRIPTION

The thiazole derivative of the present invention is represented by the following formula I

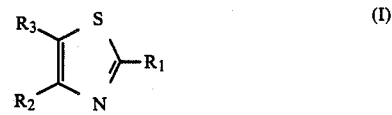

wherein
$R_1$ represents —COOR$_4$,

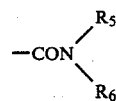

or cyano wherein
$R_4$ represents hydrogen or lower alkyl, and
$R_5$ and $R_6$ may be same or different and represent hydrogen, lower alkyl, aryl, amino-lower alkyl, N-lower alkylamino-lower alkyl, N,N-di-lower alkylamino-lower alkyl or $R_5$ and $R_6$ are joined to form N-containing heterocyclic group;
$R_2$ represents hydrogen or lower alkyl; and
$R_3$ represents N-containing heterocyclic group.

The term "lower" as used herein refers to from 1 to 6 carbon atoms unless otherwise indicated.

The term "lower alkyl" as used herein means alkyl group having from 1 to 6 carbon atoms which may be arranged as straight or branched chains. The "lower alkyl" may be methyl, ethyl, n-propyl, iso-propyl, n-butyl, iso-butyl, tert-butyl, n-pentyl, n-hexyl or the like.

The term "aryl" as used herein means aryl group which may be unsubstituted or may bear one or two substituents selected from lower alkyl, lower alkoxy (e.g. methoxy, ethoxy), halogeno (e.g. chloro, bromo), cyano, nitro, hydroxy and so on. The "aryl" may be phenyl, tolyl, xylyl, mesityl, cumenyl, biphenyl, hydroxyphenyl or the like.

The term "amino-lower alkyl" as used herein means lower alkyl group substituted with one or two of amino groups. The "amino-lower alkyl" may be aminomethyl, diaminomethyl, aminoethyl, diaminoethyl, amino-n-hexyl or the like.

The term "N-lower alkylamino-lower alkyl" as used herein means amino-lower alkyl group substituted with one lower alkyl group. The "N-lower alkylamino-lower alkyl" may be N-methylaminomethyl, N-methylaminoethyl, N-ethylaminoethyl, N-n-hexylaminoethyl or the like.

The term "N,N-di-lower alkylamino-lower alkyl" as used herein means amino lower alkyl group substituted with two lower alkyl groups. The "N,N-di-lower alkyl amino-lower alkyl" may be N,N-dimethylaminomethyl, N,N-dimethylaminoethyl, N-methyl-N-n-hexylaminomethyl or the like.

The term "N-containing heterocyclic group" as used herein means nitrogen-containing, 5 or 6 membered mono or condensed heterocyclic ring group which may be unsubstituted or may bear one or two substituents selected from lower alkyl, lower alkoxy, halogeno, cyano, nitro, aldehyde, acyl (e.g. formyl, acetyl), hydroxy and so on. The "N-containg heterocyclic group" may be pyridinil, pyridazinyl, pyrimidinyl, pyrazinyl, quinolinyl, isoquinolinyl, cinnolinyl, quanazolinyl, quinoxalinyl, phthalazinyl, acridinyl, methylpyridinyl, methoxypyrizinyl, chloropyridinyl, formylpyridinyl, cyanopyridinyl, nitropyridinyl, acetylpyridinyl, hydroxypyridinyl, methoxyquinolinyl, methylpyridazinyl, piperidino, morpholino or the like.

As to the formula I, it is to be noted that some of the compounds may be alternatively represented by its tautomers, e.g., "2-hydroxypyridinyl" and "2-oxopyridinyl". Both of said moieties are in the state of tautomeric equilibrium as represented by the following equilibriums.

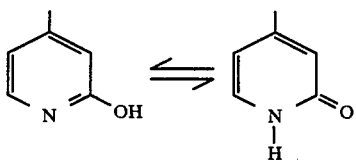

Accordingly it is to be understood that both of such isomers are included within the same category of the formula I.

In the present specification, the formula I includes the group of such tautomeric isomers which is however represented by one of the expressions.

The compounds according to the present invention are for example as follows:
methyl 4-methyl-5-(4-pyridinyl)-thiazole-2-carboxylate;
4-methyl-5-(4-pyridinyl)-thiazole-2-carboxamide;
N,4-dimethyl-5-(4-pyridinyl)-thiazole-2-carboxamide;
4-methyl-5-(4-pyridinyl)-thiazole-2-carboxanilide;
4-methyl-N-aminomethyl-5-(4-pyridinyl)-thiazole-2-carboxamide;
4-methyl-N-(2-methylaminoethyl)-5-(4-pyridinyl)-thiazole-2-carboxamide;
4-methyl-N-(2-dimethylaminoethyl)-5-(4-pyridinyl)-thiazole-2-carboxamide;
N,N-diethyl-4-methyl-5-(4-pyridinyl)-thiazone-2-carboxamide;
2',6'-dimethyl-4-methyl-5-(4-pyridinyl)-thiazole-2-carboxamide;
1-[4-methyl-5-(4-pyridinyl)-2-thiazolylcarbonyl]-piperidine;
2-cyano-4-methyl-5-(4-piperidinyl)-thiazole;
methyl 4-methyl-5-(4-pyridazinyl)-thiazole-2-carboxylate;
4-methyl-5-(4-pyridazinyl)-thiazole-2-carboxamide;
1-[4-methyl-5-(4-pyridazinyl)-2-thiazolylcarbonyl]-piperazine;
2-cyano-4-methyl-5-(4-pyridazinyl)-thiazole;
methyl 4-methyl-5-(4-quinolinyl)-thiazole-2-carboxylate;
4-methyl-5-(4-quinolinyl)-thiazole-2-carboxamide;
2-cyano-4-methyl-5-(4-quinolinyl)-thiazole;
methyl 4-methyl-5-(3-methyl-4-pyridinyl)-thiazole-2-carboxylate;
4-methyl-5-(3-methyl-4-pyridinyl)-thiazole-2-carboxamide;
2-cyano-4-methyl-5-(3-methyl-4-pyridinyl)-thiazole;
methyl 4-methyl-5-(3-acetyl-4-pyridinyl)-thiazole-2-carboxylate;
4-methyl-5-(3-acetyl-4-pyridinyl)-thiazole-2-carboxamide;
2-cyano-4-methyl-5-(3-acetyl-4-pyridinyl)-thiazole;
methyl 4-methyl-5-(3-chloro-4-pyridinyl)-thiazole-2-carboxylate;
4-methyl-5-(3-chloro-4-pyridinyl)-thiazole-2-carboxamide;
2-cyano-4-methyl-5-(3-chloro-4-pyridinyl)-thiazole;
methyl 4-methyl-5-(3-formyl-4-pyridinyl)-2-carboxylate;
4-methyl-5-(3-formyl-4-pyridinyl)-thiazole-2-carboxamide;
2-cyano-4-methyl-5-(3-formyl-4-pyridinyl)-thiazole;
methyl 4-methyl-5-(3-cyano-4-pyridinyl)-thiazole-2-carboxylate;
4-methyl-5-(3-cyano-4-pyridinyl)-thiazole-2-carboxamide;
2-cyano-4-methyl-5-(3-cyano-4-pyridinyl)-thiazole;
methyl 4-methyl-5-(6-methoxy-4-quinolinyl)-thiazole-2-carboxylate;
4-methyl-5-(6-methoxy-4-quinolinyl)-thiazole-2-carboxamide;
2-cyano-4-methyl-5-(6-methoxy-4-quinolinyl)-thiazole;
methyl 4-methyl-5-(2-thiazolyl)-thiazole-2-carboxylate;
4-methyl-5-(2-thiazolyl)-thiazole-2-carboxamide;
2-cyano-4-methyl-5-(2-thiazolyl)-thiazole;
and the like.

The thiazole derivative of the formula I is prepared according to the following process.

As to the following process, the pressure is under atmospheric pressure unless otherwise indicated.

First of all, the 2,2-di-lower alkoxy-1,4-thiazine derivative of the formula II is prepared

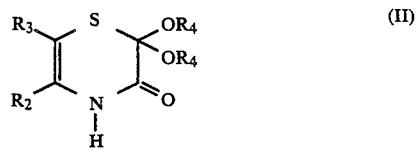

wherein $R_2$, $R_3$ and $R_4$ are as defined above.

The compound of the formula II is prepared according to the following process.

When a known 1,4-thiazine derivative of the formula VI

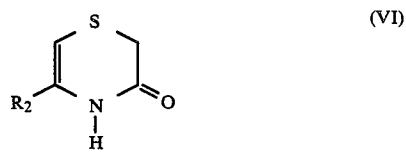

wherein $R_2$ is as defined above, is reacted with a known compound of the formula A—X' (in which A represents a residue

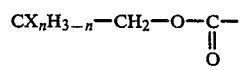

in which X represents a halogen atom and n is a number of 0 to 3, and X' represents a halogen atom which may be the same as or different from X) and a known compound of the formula $R_3$—H (in which $R_3$ is as defined above), a 1,4-thiazine derivative of the formula V is obtained.

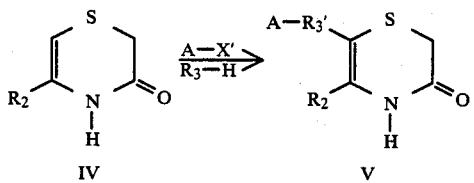

wherein $R_2$, $R_3$ and A are as defined above and $R_3'$ represents dihydro form residue of N-containing heterocyclic group.

This reaction is completed by merely stirring the compound of the formula VI, more than equal mole concentration of the compound A—X' and more than equal mole concentration of the compound of the formula $R_3$—H at room temperature for 1 to 7 hours.

The solvent, which is used in this reaction, may be nitrile such as acetonitrile, ether such as tetrahydrofran, or halogenated hydrocarbon such as dichloromethan or the like. Incidentally, the compound having N-containing heterocyclic group may also be used as a solvent.

The compound having N-containing heterocyclic group may be unsubstituted or may bear one or two substituents selected from lower alkyl, lower alkoxy, halogeno, cyano, nitro, aldehyde, acyl, hydroxy, alkoxycarbonyl and so on. The compound may be pyridine, pyridazine, pyrimidine, pyrazine, quinoline, isoquinoline, cinnoline, quinazoline, quinoxaline, phthalazine, acridine, phenazine, piperidine, piperazine, morpholine, 3-methoxypyridine, 3-chloropyridine, pyridine-3-aldehyde, nicotinonitrile, 3-acetylpyridine, methyl nicotinate, 3-nitropyridine, 3-hydroxypyridine, 6-methoxyquinoline, 3-methylpyridazine or the like.

Then the compound of the formula IV is obtained by aromatization of the compound of the formula V. This may be effected in various processes; a preferred process is as follows.

The compound of the formula V is reacted with sulfur at elevated temperature to obtain the 1,4-thiazine derivative of the formula IV.

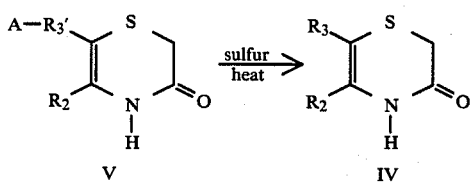

wherein $R_2$, $R_3$, A and $R_3'$ are as defined above.

This reaction proceeds well by stirring the compound of the formula V with from half to 5 fold amount of sulfur and heating the mixture at 120° to 200° C. for 0.5 to 8 hours. Generally, no solvent is needed in this reaction; however, N,N-dimethylformamide, dimethyl sulfoxide, xylene, (o-, m-, p-) dichlorobenzene, diglime, etc. may be employed.

Alternatively, the compound of the formula IV may be prepared according to a process that the compound of the formula V is reacted with zinc at room temperature or elevated temperature. Some of the compound of the formula V is reacted with zinc to obtain thiazole derivative having dihydro form residue of N-containing heterocyclic group at position 6. In this case, it is necessary to oxidize a reaction intermediate by an oxidizing agent. This process is represented by the following formula

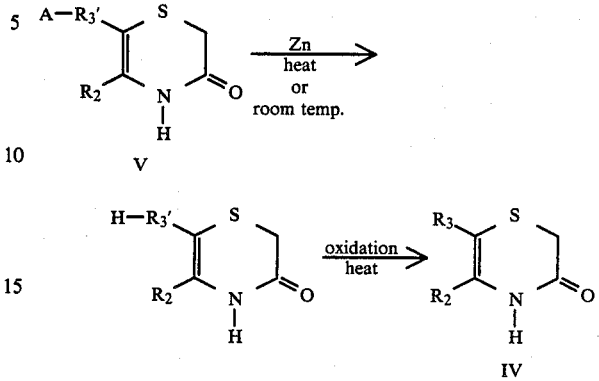

wherein $R_2$, $R_3$, A and $R_3'$ are as defined above.

This reaction proceeds well by stirring the compound of the formula V with excessive amount of zinc and stirring the mixture at room temperature or elevated temperature up to 80° C. for 1 to 4 hours. A solvent used in this reaction may be an organic solvent in the form of mixture with water; the organic solvent may be carboxylic acid such as formic acid, nitrile such as acetonitrile, ether such as tetrahydrofuran, sulfoxide such as dimethylsulfoxide or amide such as methylformamide or the like. The oxidizing agent used in this reaction may be 2,3-dichloro-5,6-dicyanobenzoquinone (DDQ) or the like.

Purification of the compounds of the formula V and VI may be accomplished by recrystallization from lower alcohol such as methanol, ethanol or isopropanol, ketone such as acetone, halogenated hydrocarbon such as chloroform, carboxylic acid ester such as ethyl acetate, aromatic hydrocarbon such as benzene, ether such as diethylether or nitrile such as acetonitrile or the like.

Alternatively, such purification may also be accomplished by column chromatography or thin layer chromatography. In this operation, silica gel having particles size of 100–200 mesh such as Wakogel C-200 (manufactured by Wako Junyaku Kabushiki Kaisha in Japan), silica gel having particle's average porous diameter of 40–63 μm such as silica gel 650 Lichloprep 60 (manufactured by Merck & Co. Inc. in USA) or fluoresces a light blue color in the region of 254 nm such as Merch TCL plate silica gel 60F$_{254}$ (manufactured by Merck & Co. Inc. in USA) is preferable to use.

Incidentally, the compound of the formula C may be directly used in the subsequent reaction without purification.

The known starting material 1,4-thiazine derivative of the formula VI may be prepared according to the processes proposed by H. Sokol et al. in J. Am. Chem. Soc., 70, 3517 (1948), C. R. Johnson et al. in J. Heterocycl. Chem., 6, 247-249 (1969), and G. V. Rao et al. in Synthesis, 136 (1972).

Then, the thiazine derivative having substituent group such as lower alkoxy, halogeno, acyloxy or hydroxy or the like at position 2 may be prepared according to the process by M. Hojo et al. in Synthesis 312, 426 (1982).

Thus, the compound of the formula IV is reacted with the compound of the formula A'—COOOH (in which A' represent lower alkyl, alicyclic residue or aryl), i.e. peroxycarboxylic acid to obtain the compound of the formula III.

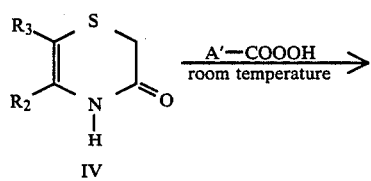

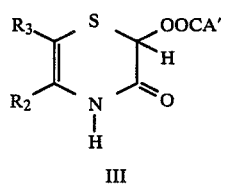

wherein $R_2$, $R_3$ and $A'$ are as defined above.

This reaction is completed by merely stirring the compound of the formula IV and more than equal mole concentration of the compound of the formula $A'$—COOOH under ice-cooling for a few minutes.

The solvent, which is used in this reaction, may be halogenated hydrocarbon such as dichloromethane, nitrile such as acetonitrile, ether such as tetrahydrofuran, sulfoxide such as dimethylsulfoxide or amide such as dimethylformamide or the like.

As for the peroxycarboxylic acid, aliphatic peroxycarboxylic acid such as performic acid or peracetic acid, alicyclic peroxycarboxylic acid such as cyclohexaneperoxycarboxylic acid, or aromatic peroxycarboxylic acid such as perbenzoic acid or monoperoxyphthalic acid may be employed. The peroxycarboxylic acid having substituent such as lower alkyl, lower alkoxy, halogeno, cyano, nitro, aldehdye, acyl, hydroxy or the like may also be employed. In view of the state of the reaction system (the reactivity and degree of dissociation) and the easy availability, m-chloroperbenzoic acid is especially preferred.

Then, the compound of the formula III is reacted with the nucleophilic reagent of the formula $R_4$—OH (in which $R_4$ is as defined above) to obtain the compound of the formula II'.

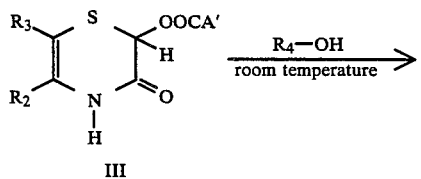

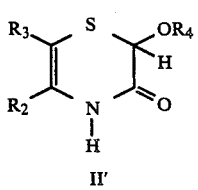

wherein $R_2$, $R_3$, $R_4$ and $A'$ are as defined above.

This reaction is completed by merely stirring the compound of the formula III and more than equal mole concentration of the compound of the formula $R_4$—H at room temperature for more than 1 day. Alternatively, the reaction may be carried out at 50°–70° C.

In this raection, the compound of the formula $R_4$—H may be used as a solvent.

Incidentally, amide such as dimethylformamide, nitrile such as acetonitrile, ether such as tetrahydrofuran, sulfoxide such as dimethylsulfoxide or halogenated hydrocarbon such as dichloromethane or the like may be used as a solvent.

As for the compound of the formula $R_4$—OH, lower alcohol such as methanol, ethanol, iso-propanol or the like may be employed.

Then, the compound of the formula II' is reacted with more than equal mole concentration of the formula $A'$—COOOH and more than two mole concentration of the formula $R_4$—OH to obtain the compound of the formula II.

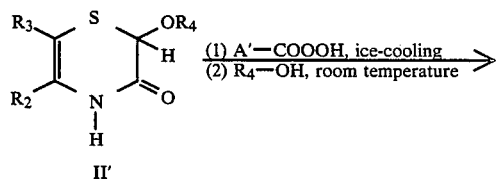

wherein $R_2$, $R_3$, $R_4$ and $A'$ are as defined above.

The compound of the formula III, the compound of the formula II' and the compound of the formula II may be used in the subsequent reaction without purification.

Incidentally, purification of these compounds may be accomplished by recrystallization from lower alcohol such as methanol, ethanol or isopropanol, halogenated hydrocarbon such as chloroform or carboxylic acid ester such as ethyl acetate or the like.

Alternatively, such purification may also be accomplished by alumina column chromatography. In this operation, alumina having 300 mesh is preferable to use. And, halogenated hydrocarbon such as chloroform or carboxylic acid ester such as ethyl acetate or the like may be used as an eluent.

The thiazine derivative having substituent at position 2, i.e. the compound of the formula II, may be also obtained by the following process. One mole concentration of the compound of the formula IV is reacted with more than two mole concentration of the compound of the formula $A'$—COOOH and more than two mole concentration of the compound of $R_4$—OH in a similar manner as above.

Alternatively, the compound of the formula II may be obtained by introduction of —$OR_4$ group position at 2 in the same manner as above, then introduction of —$R_3$ group position at 6 in the same manner as above.

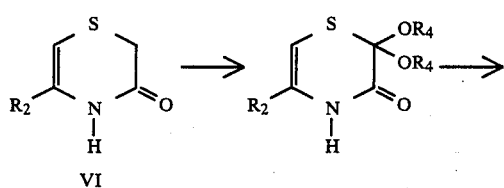

VI

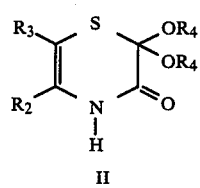

II wherein, $R_2$, $R_3$, $R_4$ are as defined above.

The compound of the formula II is reacted with an acid to obtain the compound of the formula I' i.e. thiazole derivative having lower alkoxycarbonyl group at position 2.

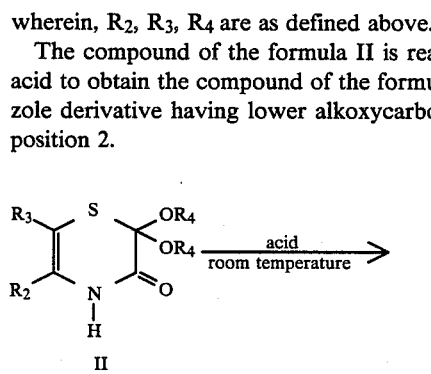

where $R_2$, $R_3$ and $R_4$ are as defined above.

This reaction is completed by merely allowing the compound of the formula II with more than equal mole concentration of the acid and the mixture to stand at room temperature for more than 10 minutes. The acid used in this reaction may be inorganic acid such as hydrochloric acid, sulfuric acid, etc. or organic acid such as acetic acid, etc. In view of the state of the reaction system (the reactivity and degree of dissociation) and the easy availability, hydrochloric acid is especially preferred.

This reaction is proceeded by adding the compound of the formula II into the acid which is diluted with water.

The solvent used in this reaction is water.

Purification of the compound of the formula I' may be accomplished by recrystallization from aromatic hydrocarbon such as benzene or alicyclic hydrocarbon such as cyclopentane, cyclohexane or the like or a mixture of two or more of these solvents.

Alternatively, such purification may be accomplished by column chromatography or thin layer chromatography.

Optionally, the —COOR$_4$ group (in which R$_4$ is as defined above) of the compound of the formula I' may be converted into

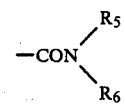

group (in which $R_5$ and $R_6$ are as defined above) or cyano group by methods known in the art. Thus the compound of the formula I'', i.e. thiazole derivative having unsubstituted or substituted aminocarbonyl group at position 2, is prepared by reacting the compound of the formula I' with the compound of the formula

(in which $R_5$ and $R_6$ are as defined above).

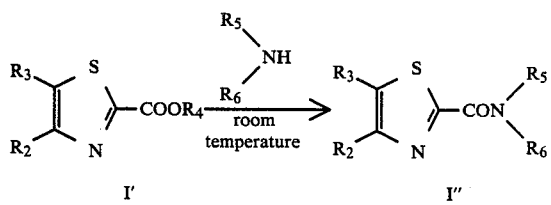

wherein $R_2$, $R_3$, $R_4$, $R_5$ and $R_6$ are as defined above.

This reaction is completed by merely stirring the compound of the formula I' and more than equal mole concentration of the compound of the formula

at room temperature for more than 1 hour, preferably about 10 hours.

Alternatively, it may be completed by once converting the compound of the formula I' into a reaction intermediate having chlorocarbonyl group and then reacting the same with the compound of the formula

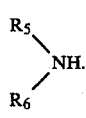

More specifically, first, the compound of the formula I' and a base such as sodium hydroxide aqueous solution or potassium hydroxide aqueous solution are stirred at room temperature to obtain a thiazole derivative having carboxy group at postion 2. Secondly, the compound having carboxy group at position 2 and more than equal mole of chlorination agent such as thionyl chloride are stirred at room temperature for more than 10 hours to obtain a thiazole derivative having chlorocarbonyl group at position 2. Thirdly, the compound having chlorocarbonyl group at position 2 is reacted with more than equal mole of the compound of the formula

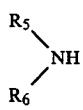

at room temperature for more than 10 hours to obtain the compound of the formula I'. This process is represented by the following formula

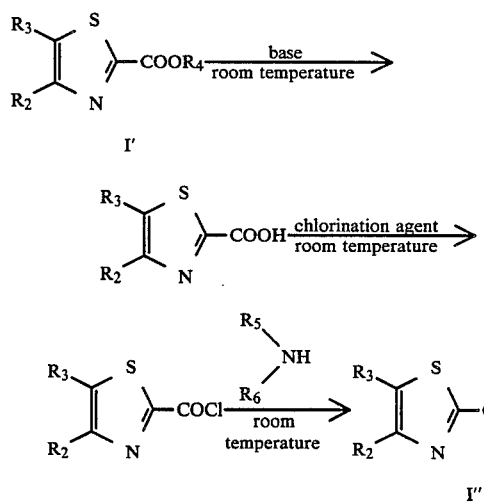

wherein $R_2$, $R_3$, $R_4$, $R_5$ and $R_6$ are as defined above.

As for the compound represented by the formula

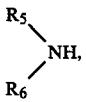

ammonia water, lower alkyl amine such as methylamine or ethylamine, aromatic amine such as aniline, toluidine or xylidine, di-amine such as N,N-dimethylaminoethylamine, secondary amine such as N,N-dimethylamine, N,N-diethylamine or heterocyclic compound having nitrogen atoms such as piperidine, piperazine or morpholine or the like may be used in this reaction. As for the solvent, lower alcohol such as methanol or ethanol, ether such as tetrahydrofuran, aromatic hydrocarbon such as toluene or xylene or water or the like may be used in this reaction.

Alternatively, the compound of the formula

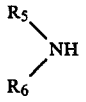

may be used as a solvent.

Purification of the compound of the formula I" may be accomplished by recrystallization from lower alcohol such as methanol, ethanol or iso-propanol, aromatic hydrocarbon such as benzene, alicyclic hydrocarbon such as cyclopentane or cyclohexane, ether such as tetrahydrofuran or a mixture of two or more of these solvents or the like.

Alternatively, it may be accomplished by silica gel column chromatography or silica gel thin layer chromatography.

The compound of the formula I''', i.e. the thiazole derivative having cyano group at position 2, is obtained by treating the compound of the formula I'', especially 2-carbamoylthiazole derivative in which $R_5$ and $R_6$ are hyrogen atoms, with a dehydrating agent in the usual way. More specifically, the reaction is completed by stirring the compound of the formula I'' and more than equal mole of a dehydrating agent such as p-toluenesulfonyl chloride or phosphorus trichloride at 60° to 120° C. for about 20 hours. It is preferable to conduct this reaction in the presence of a base such as pyridine.

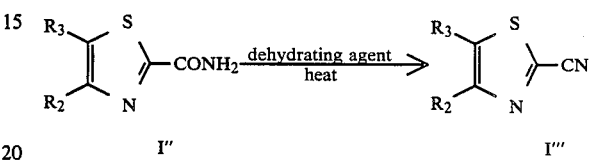

wherein $R_2$ and $R_3$ are as defined above.

Amide such as N,N-dimethylformamide, ether such as tetrahydrofuran or heterocyclic compound having nitrogen atom such as pyridine is employed as a solvent.

Purification of the compound of the formula I''' may be accomplished by recrystallization from halogenated hydrocarbon such as chloroform or lower alcohol such as methanol, ethanol or iso-propanol.

Alternatively, it may be accomplished by silica gel column chromatography or thin layer chromatography.

When the known thioamide of the formula VIII (in which $R_1$ and $R_3$ are as defined above) is reacted with the known halocarbonyl compounds of the formula VII (in which $R_2$ is as defined above and X" represents halogen atom) according to the process proposed by Richard H. Willey in Organic Reaction 6 382 (1951), the compound of the formula I may be also obtained.

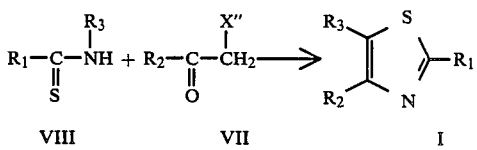

wherein $R_1$, $R_2$, $R_3$ and X" are as defined above.

However, with this known method, the compound of the formula I is obtained in lower yield. This method is unsuitable as industrial process.

The compound of the formula I may be converted into a pharmaceutically acceptable salt by using an appropriate acid.

The appropriate acids which may be used include, for example, inorganic acid such as hydrochloric, hydrobromic, sulfuric, nitric or phosphoric acid, or organic acid such as acetic, propionic, glycolic, lactic, pyruvic, malonic, succinic, maleic, fumaric, malic, tartaric, citric, benzoic, cinnomic, manderic, methanesulfonic, hydroxyethanesulfonic, benzenesulfamic, p-toluenesulfamic, cyclohexanesulfamic, salicylic, p-aminosalicylic, 2-phenoxybenzoic or 2-acetoxybenzoic acid.

The pharmacological effects of the compound of the formula I will now be described;

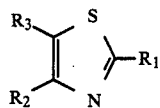

wherein $R_1$, $R_2$ and $R_3$ are as defined above.

(1) The contractile force of left atrium was tested according to the method described in Basic Lectures of Medicine Development, Volume V, Pharmacological Test Methods, Part 2, page 535 (1971). A 7-weeks-old male Hartley guinea pig (having a bodyweight of about 350 g) was killed by a blow on a head. The chest was opened and the heart was removed and placed in Krebs-Henseleit solution (prepared by adding distilled water to 6.92 g of sodium chloride, 0.35 g of calcium chloride, 0.29 g of magnesium sulfate, 0.16 g of mono-basic potassium phosphate, 2.1 g of sodium bicarbonate and 1.8 g of glucose so that the total amount was 1 l) which sufficiently bubbled with oxygen gas. Threads were tied to each tip of the left atrium. One thread was attached to a fixed pin in Magnus's bath and the other to a force-displacement transducer connected to an electric amplifier and recorder. The atrium was stimulated electrically at 0.5 cps, 5 msec and a voltage of 20% above threshold. The preparation is mounted in Krebs-Henseleit solution through which 95% oxygen gas and 5% carbon dioxide was blown. Then the samples were added. The results are shown in Table 1.

TABLE 1

Effect on Contractile Force of Isolated Left Atrium

| The compound of the formula I | Corresponding Concentration (mol) | Maximum Contractile Force (mg) |
| --- | --- | --- |
| $R_1 = -COOCH_3$, $R_2 = -CH_3$, $R_3 = 4$-pyridinyl | $1 \times 10^{-4}$ | $446 \pm 91$ |
| $R_1 = -CONH_2$, $R_2 = -CH_3$, $R_3 = 4$-pyridinyl | $1 \times 10^{-4}$ | $1,325 \pm 132$ |
| $R_1 = -CONHCH_3$, $R_2 = -CH_3$, $R_3 = 4$-pyridinyl | $1 \times 10^{-4}$ | $510 \pm 45$ |
| $R_1 = -CN$, $R_2 = -CH_3$, $R_3 = 4$-pyridinyl | $1 \times 10^{-4}$ | $558 \pm 123$ |

(2) The acute toxicity of the compound of the formula I was determined according to the Litchfield-Wilcoxon method, J. Pharm. Exp. Ther., 96, 99 (1949) using 6-weeks-old male ddY mice (having a bodyweight of 19-24 g) while administrating the sample compound in intraperitonial injection. The results are shown in Table 2.

TABLE 2

Acute Toxicity Test Result

| The compound of the formula I | $LD_{50}$ (mg/kg) |
| --- | --- |
| $R_1 = -CONH_2$, $R_2 = -CH_3$, $R_3 = 4$-pyridinyl | 230 |

From the above test results, it was confirmed that the contractile force of isolated left atrium was significantly increased by administration of the compound of the formula I, and the acute toxicity of the compound of the formula I is low.

The compound of the formula I may be administered to human body orally, by injection (intravenously, subcutaneously or intramuscularly) or in any other manner. When the compound of the formula I is in the form of solid preparations for oral administration, the preparations may be tablets, granules, powders, capsules or the like. The preparations may contain additives, for example, an excipient such as a saccharide or cellulose preparation, a binder such as starch paste or methyl cellulose, a filler, a disintegrator and so on, all being ones usually used in manufacture of medical preparations.

In case the compound of the formula I is employed as oral liquid preparations, they may be of any form selected from aqueous preparations for internal use, suspensions, emulsions, syrups, etc., and further they may be in the form of dried products which are dissolved prior to the use.

The compound of the formula I may be injected in the form of aqueous solutions, suspensions or oily or aqueous emulsions, but usually the injections are prepared by dissolving or suspending them in aqueous liquid media such as sterile water of physiological saline solutions.

If necessary, conventionally used dissolving agents, stabilizers, preservatives, additives for preparing isotonic solutions, etc. may be added to the injections.

Further, the above-mentioned tests were carried out by using following apparatuses.

Magnus's bath: supplied by Kabushiki Kaisha Natsume Seisakusho

Recorder: Model WI-680G supplied by Nippon Koden Kabushiki Kaisha

Force displacement transducer: supplied by Nippon Koden Kabushiki Kaisha

Electrical amplifier: Model AP-600G supplied by Nippon Koden Kabushiki Kaisha

Programmed electrosphygmonometer: supplied by Nippon Koden Kabushiki Kaisha

The invention will be understood more readily with reference to the following examples; however these examples are intended to illustrate the invention and are not to be constituted to limit the scope of the invention. In the examples, the measurements were carried out by using the following apparatuses.

Melting point: Model MP-1 supplied by Yamato Kagaku Kabushiki Kaisha

Mass analysis: Model M-60 supplied by Kabushiki Kaisha Hitachi Seisakusho

Infrared absorption spectrum (IR): Model 260-10 supplied by Kabushiki Kaisha Hitachi Seisakusho Nuclear magnetic resonance (NMR): Model FX-270 supplied by Nippon Denshi Kabushiki Kaisha Elementary analysis: Model MT-2 supplied by Kabushiki Kaisha Yanagimoto Seisakusho

EXAMPLE 1

Methyl 4-methyl-5-(4-pyridinyl)-thiazole-2-carboxylate (i) Preparation of intermediate, 5-methyl-6-[1-(2,2,2-trichloroethoxycarbonyl)-1,4-dihydro-4-pyridinyl]-2H-1,4-thiazin-3(4H)-one 2,2,2-Trichloroethylchloroformate (64 ml) was added dropwise to a stirred suspension of 5-methyl-2H-1,4-thiazin-3(4H)-one (50 g) in a mixture of acetonitrile (500 ml)-pyridine (75 ml) under ice-cooling. The mixture was stirred at room temperature for 1 hour and then, poured into cold water (1.5 l) The resulting precipitates were collected by filtration, recrystallized from ethanol to give 5-methyl-6-[1-(2,2,2-trichloroethoxycarbonyl)-1,4-dihydro-4-pyridinyl]-2H-1,4-thiazin-3(4H)-one (120 g, yield 80.7%) as pale yellow prisms.

Melting point: 158°–160° C.

Elementary analysis values as: $C_{13}H_{13}N_2O_3SCl_3$; Calculated: C=40.69, H=3.41, N=7.29 (%). Found: C=40.62, H=3.37, N=7.02 (%).

Mass spectrum: M+382.

NMR spectrum (CDCl$_3$, TMS) δ: 1.986 (3H, s), 3.229 (2H, s), 4.161 (1H, m), 4.800 (4H, m), 6.970 (2H, d), 7.264 (1H, b).

IR spectrum $\nu_{max}^{KBr}$(cm$^{-1}$): 3200, 3100, 1720, 1670, 1630.

(ii) Preparation of intermediate, 5-methyl-6-(4-pyridinyl)-2H-1,4-thiazin-3(4H)-one (A) The mixture of 5-methyl-6-[1-(2,2,2-trichloroethoxycarbonyl)-1,4-dihydro-4-pyridinyl]-2H-1,4-thiazin-3(4H)-one (2.14 g) and sulfur (10.7 g) was stirred at 140° C. for 1.5 hours and then cooled to room temperature. The obtained solid was extracted with methanol by using Soxhlet extractor. Methanol was evapolated to dryness, and the residue was dissolved in 50 ml of 2N hydrochloric acid. The insoluble solid was removed by filtration and the filtrate was adjusted to pH 7.2 by addition of 2N sodium hydroxide aqueous solution. The precipitates were collected by filtration and the filtrate was extracted with chloroform (20 ml×5 times) and was evaporated to dryness. The combined precipitates and the residue were recrystallized from isopropanol to give 5-methyl-6-(4-pyridinyl)-2H-1,4-thiazin-3(4H)-one (0.88 g, yield 76.5%) as pale yellow plates.

Melting point: 187°–188.5° C. (decomposition).

Elementary analysis values as: $C_{10}H_{10}N_2OS$; Calculated: C=58.22, H=4.88, N=13.58 (%). Found: C=58.48, H=4.99, N=13.53 (%).

Mass spectrum: M+206.

NMR spectrum (CDCl$_3$, TMS) δ: 2.05 (3H, s), 3.43 (2H, s), 7.28 (2H, d), 8.61 (2H, d), 8.70 (1H, s).

IR spectrum $\nu_{max}^{KBr}$(cm$^{-1}$): 3200, 3050, 1680, 1580.

(B) Zinc powder (1 g) was added to a stirred solution of 5-methyl-6-[1-(2,2,2-trichloroethoxycarbonyl)-1,4-dihydro-4-pyridinyl]-2H-1,4-thiazin-3(4H)-one (1 g) in formic acid (14 ml), and the reaction mixture was stirred at room temperature for 3 hours. The insoluble solid was removed by filtration. The filtrate was evaporated to dryness and the residue was dissolved in water (30 ml). The solution was adjusted to pH 7.0 by addition of 1N sodium hydroxide aqueous solution. The precipitates were extracted with chloroform (although the solution was converted into an emulsion at this extracting step, the operation was facilitated by using a filter aid such as "Avicel"). The extract was dried over anhydrous magnesium sulfate and was evaporated under reduced pressure. The crude product was purified by the preparative thin layer chromatography [Merck TLC plate, silica gel 60F$_{254t}$ (particles average porous diameter 60A, Fluorescent substance Zn$_2$SiO$_4$/Mn), 20×20 cm, t=1 mm, chloroform/methanol=20/1] to give 200 mg of 5-methyl-6-(4-pyridinyl)-2H-1,4-thiazin-3(4H)-one. The physical properties were as described above.

(iii) Preparation of intermediate, 2,2-dimethoxy-5-methyl-6-(4-pyridinyl)-2H-1,4-thiazin-3-(4H)-one m-Chloroperbenzoic acid (5.4 g) was added to a stirred suspension of 5-methyl-6-(4-pyridinyl)-2H-1,4-thiazin-3(4H)-one (4.5 g) in methanol (180 ml) under ice-cooling, and the mixture was stirred at room temperature for 3 days. The mixture was evaporated to dryness and the residue was extracted with ethyl acetate, and was washed with sodium bicarbonate aqueous solution and water, dried over magnesium sulfate and concentrated under reduced pressure. The residue was chromatographed on activated alumina column (100 g, 300 mesh, manufactured by Wako Junyaku Kabushiki Kaisha) and eluted with chloroform (30 ml). The eluate was concentrated under reduced pressure and the residue was washed with ether (100 ml), and was collected by filtration. m-Chloroperbenzoic acid (2.8 g) was added to a stirred solution of the resulting precipitates in methanol (100 ml) at room temperature, and the reaction mixture was stirred at room temperature for 2 hours. The reaction mixture was evaporated to dryness and the residue was dissolved in ethyl acetate. The extract was washed with sodium bicarbonate aqueous solution and successively with water, dried over magnesium sulfate and concentrated under reduced pressure. The residue was washed with ether, and the resulting powder was collected by filtration to give 2,2-dimethoxy-5-methyl-6-(4-pyridinyl)-2H-1,4-thiazin-(4H)-one (2 g, yield 35.0%) as pale yellow powder.

Melting point: 154°–155° C.

NMR spectrum (CDCl$_3$, TMS) δ: 2.03 (3H, s), 3.59 (6H, s), 7.25 (2H, dd), 8.43 (1H, s), 8.62 (2H, dx2).

(iv) Preparation of methyl 4-methyl-5-(4-pyridinyl)-thiazole-2-carboxylate 2,2-Dimethoxy-5-methyl-6-(4-pyridinyl)-2H-1,4-thiazin-3(4H)-one (200 mg) was dissolved in 2N hydrochloric acid (2 ml), and the mixture was allowed to stand at room temperature for 30 minutes. Then, the solution was made alkaline by addition of 2N aqueous sodium hydroxide under ice-cooling, and the resulting precipitates were collected by filtration. The precipitates were washed with water, air-dried, and was recrystallized from benzene-petroleum ether to give methyl 4-methyl-5-(4-pyridinyl)-thiazole-2-carboxylate (158 mg, yield 90%) as colorless needles.

Melting point: 121°–123° C.

Elementary analysis values as: $C_{11}H_{10}N_2O_2S$; Calculated: C=56.39, H=4.30, N=11.95 (%). Found: C=56.33, H=4.29, N=11.62 (%).

Mass spectrum: M+234.

NMR spectrum (CDCl$_3$, TMS) δ: 2.65 (3H, s), 4.04 (3H, s), 7.40 (2H, dd), 8.72 (2H, dx2).

IR spectrum $\nu_{max}^{KBr}$(cm$^{-1}$): 1750, 1720, 1600.

In the same manner as described in Example 1 (i)–(iv), the compounds of Example 2 to 4 are obtained.

EXAMPLE 2

Methyl 4-methyl-5-(3-methyl-4-pyridinyl)-thiazole-2-carboxylate

5-Methyl-2H-1,4-thiazine-3(4H)-one was treated with 3-methyl-pyridine to give methyl 4-methyl-5-(3-methyl-4-pyridinyl)-thiazole-2-carboxylate as colorless prisms.

Melting point: 95.5°–96.3° C.

NMR spectrum (CDCl$_3$, TMS) δ: 2.24 (3H, s), 2,37 (3H, s), 4,04 (3H, s), 7,19 (1H, d), 8.54 (1H, d), 8.60 (1H, s).

IR spectrum $\nu_{max}^{KBr}$(cm$^{-1}$): 1735.

EXAMPLE 3

Methyl 4-methyl-5-(3-cyano-4-pyridinyl)-thiazole-2-carboxylate

5-Methyl-2H-1,4-thiazine-3(4H)-one was treated with 3-cyano-pyridine to give methyl 4-methyl-5-(3-cyano-4-pyridinyl)-thiazole-2-carboxylate as colorless columns.

Melting point: 193°–194° C.

NMR spectrum (CDCl$_3$, TMS) δ: 2.55 (3H, s), 4.05 (3H, s), 7.47 (1H, d), 8.90 (1H, d), 9.03 (1H, s).

IR spectrum $\nu_{max}^{KBr}$(cm$^{-1}$): 2230, 1710.

EXAMPLE 4

Methyl 4-methyl-5-(4-quinolinyl)-thiazole-2-carboxylate

5-Methyl-2H-1,4-thiazine-3(4H)-one was treated with quinoline to give methyl 4-methyl-5-(4-quinolinyl)-thiazole-2-carboxylate as colorless granules.

Melting point: 116°–117° C.

NMR spectrum (CDCl$_3$, TMS) δ: 2.37 (3H, s), 4.07 (3H, s), 7.41 (1H, d), 7.60–8.23 (4H, m), 9.01 (1H, d).

IR spectrum $\nu_{max}^{KBr}$(cm$^{-1}$): 1730, 1710.

EXAMPLE 5

4-Methyl-5-(4-pyridinyl)-thiazole-2-carboxamide

Methyl 4-methyl-5-(4-pyridinyl)-thiazole-2-carboxylate (3 g) was added to a stirred ammonia (28%, 85 ml) at room temperature, and the mixture was stirred at room temperature for overnight. The resulting precipitate was collected by filtration, washed with water, and air dried. The precipitate were recrystallized from ethanol to give 4-methyl-5-(4-pyridinyl)-thiazole-2-carboxyamide (2.3 g, yield 82%) as pale yellow needles.

Melting point: 222.5°–224° C.

Elementary analysis values as: C$_{10}$H$_9$N$_3$OS; Calculated: C=54.77, H=4.13, N=19.16 (%). Found: C=54.77, H=4.11, N=18.73 (%).

Mass spectrum: M+219.

IR spectrum $\nu_{max}^{KBr}$(cm$^{-1}$): 3450, 3200, 1670, 1580.

EXAMPLE 6

N,4-Dimethyl-5-(4-pyridinyl)-thiazole-2-carboxamide

Methyl amine (0.5 ml) was added to a stirred solution of methyl 4-methyl-5-(4-pyridinyl)-thiazole-2-carboxylate (250 mg) in absolute ethanol (10 ml) at room temperature, and the mixture was stirred at room temperature for overnight. The mixture was evaporated to dryness and the residue was recrystallized from isopropanol to give N,4-dimethyl-5-(4-pyridinyl)-thiazole-2-carboxamide (200 mg, yield 80.0%) as pale yellow needles.

Melting point: 184°–186° C.

Elementary analysis values as: C$_{11}$H$_{11}$N$_3$OS; Calculated: C=56.63, H=4.75, N=18.01 (%). Found: C=56.69, H=4.80, N=17.50 (%).

NMR spectrum (CDCl$_3$, TMS) δ: 2.56 (3H, s), 3.04 (3H, d), 7.26 (1H, b), 7.40 (2H, dd), 8.70 (2H, dx2).

IR spectrum $\nu_{max}^{KBr}$(cm$^{-1}$): 3200, 3100, 1670, 1600.

EXAMPLE 7

4-Methyl-5-(4-pyridinyl)-thiazole-2-carboxanilide n-Butyllithium (14–17% in hexane, 1.2ml) was added to dropwise a stirred solution of aniline (0.12 ml) in dry tetrahydrofuran (3 ml) at room temperature under nitrogen atmosphere. Then, methyl 4-methyl-5-(4-pyridinyl)-thiazole-2-carboxylate (200 mg) was added to a stirred solution at room temperature under nitrogen atmosphere, and the mixture was stirred in the same condition for 1 hour. The resulting precipitates were collected by filtration, and the precipitates were washed with water, and air-dried. The precipitate was recrystallized from benzenepetroleum ether to give 4-methyl-5-(4-pyridinyl)-thiazole-2-carboxanilide (80 mg, yield 33.3%) as colorless plates.

Melting point: 196°–197° C.

Elementary analysis values as: C$_{16}$H$_{13}$N$_3$OS; Calculated: C=65.06, H=4.43, N=14.22 (%). Found: C=64.98, H=4.43, N=13.82 (%).

NMR spectrum (CDCl$_3$, TMS) δ: 2.62 (3H, s), 7.18–7.43 (5H, m), 7.75 (2H, dd), 8.72 (2H, dx2), 9.05 (1H, s).

IR spectrum $\nu_{max}^{KBr}$(cm$^{-1}$): 3220, 3100, 1660, 1590.

EXAMPLE 8

4-Methyl-N-(2-dimethylaminoethyl)-5-(4-pyridinyl)-thiazole-2-carboxamide hydrochloride N,N-Dimethylethylenediamine (1.4 ml) was added to a suspension of methyl 4-methyl-5-(4-pyridinyl)-thiazole-2-carboxylate (200 mg) in water (2.8 ml) at room temperature, and the mixture was stirred at room temperature for overnight. The mixture was evaporated to dryness and the residue was chromatographed on an activated alumina column and eluted with chloroform to give 4-methyl-N-(2-dimethylaminoethyl)-5-(4-pyridinyl)-thiazole-2-carboxamide as yellow oil.

IR spectrum $\nu_{max}^{KBr}$(cm$^{-1}$): 3200, 1650, 1590, 1530.

4-Methyl-N-(2-dimethylaminoethyl)-5-(4-pyridinyl)-thiazole-4-carboxamide was adjusted to pH 1 to 2 by addition of conc. hydrochloric acid, and the solution was evaporated to dryness. The residue was washed with ethanol to give 4-methyl-N-(2-dimethylaminoethyl)-5-(4-pyridinyl)-thiazole-2-carboxamide hydrochloride as colorless powder.

Melting point: over 220° C. (decomposition).

Elementary analysis values as: C$_{14}$H$_{20}$N$_4$OSCl$_2$.2-H$_2$O; Calculated: C=43.18, H=6.21, N=14.39 (%). Found: C=43.62 H=5.74, N=14.38 (%).

NMR spectrum (DMSO-d$_6$, TMS) δ: 2.67 (3H, s), 2.81 (3H, s), 2.83 (3H, s), 3.30 (2H, m), 3.70 (2H, m), 8.15 (2H, dd), 8.95 (2H, dx2), 9.24 (1H, t).

EXAMPLE 9

N,N-diethyl-4-methyl-5-(4-pyridinyl)-thiazole-2-carboxamide (i) Preparation of 4-methyl-5-(4-pyridinyl)-thiazole-2-carboxylic acid Potassium hydroxide (1 g) was added to a stirred solution of methyl 4-methyl-5-(4-pyridinyl)-thiazole-2-carboxylate (2 g) in methanol (50 ml) at room temperature and the mixture was stirred at room temperature for 1.5 hours, diluted with water (150 ml), and washed with chloroform. Then the solution was adjusted to pH 3 to 4 by addition of 2N hydrochloric acid aqueous solution. The resulting precipitate was collected by filtration, and air-dried to give 4-methyl-5-(4-pyridinyl)-thiazole-2-carboxylic acid (1.8 g, 96%) as colorless powder.

Melting point: 133°–134° C. (decomposition)

Elementary analysis values as: C$_{10}$H$_8$N$_2$O$_2$S; Calculated: C=54.33, H=3.66, N=12.72 (%). Found: C=53.95, H=3.54, N=12.37 (%).

IR spectrum $\nu_{max}^{KBr}$(cm$^{-1}$): 1705, 1630, 1610, 1520.

(ii) Preparation of N,N-diethyl-4-methyl-5-(4-pyridinyl)-thiazole-2-carboxamide

Catalytic amount of N,N-dimethylformamide in thionyl chloride (2 ml) is added to a stirred solution of 4-methyl-5-(4-pyridinyl)-thiazole-2-carboxylic acid (100 mg) at room temperature for overnight. The mixture was evaporated to dryness. Diethylamine (1 ml) was added to a stirred solution of the mixture in dry toluene (2 ml), and the reaction mixture was stirred at room temperature for overnight. The reaction mixture was diluted with ethyl acetate, washed with water, dried over magnesium sulfate, and evaporated to dryness. The residue was washed with petroleum ether, and was chromatographed on a flash column and eluted with ethyl acetate-n-hexane=6:4 to give N,N-diethyl-4-methyl-5(4-pyridinyl)-thiazole-2-carboxamide (60 mg, yield 48%) as colorless needles.

Melting point: 87.5°–89° C.

Elementary analysis values as: $C_{14}H_{17}N_3OS$; Calculated: C=61.06, H=6.22, N=15.26 (%). Found: C=60.68, H=6.25, N=14.62 (%).

NMR spectrum (CDCl$_3$, TMS) δ: 1.3 (6H, t), 2.6 (3H, s), 3.3–4.4 (4H, m), 7.5 (2H, dd), 8.8 (2H, dx2).

IR spectrum $\nu_{max}^{KBr}$(cm$^{-1}$): 1610, 1590.

EXAMPLE 10

2',6'-dimethyl-4-methyl-5-(4-pyridinyl)-thiazole-2-carboxanilide 2,6-Dimethyl aniline hydrochloride (230 mg) was added to a stirred suspension of 4-methyl-5-(4-pyridinyl)-thiazole-2-carbonylchloride hydrochloride (230 mg) in dry toluene (4 ml) at room temperature, and triethylamine (1.8 ml) was added to the mixture, and was stirred at room temperature for overnight. The mixture was diluted with chloroform, washed with water, dried over magnesium sulfate, and evaporated to dryness. The residue was recrystallized from iso-propanol to give 2',6'-dimethyl-4-methyl-5-(4-pyridinyl)-thiazole-2-carboxanilide (180 mg, yield 31%) as colorless plates.

Melting point: 192°–194° C.

Elementary analysis values as: $C_{18}H_{17}N_3OS$; Calculated: C=66.84, H=5.29, N=12.99 (%). Found: C=66.30, H=5.30, N=12.43 (%).

NMR spectrum (CDCl$_3$, TMS) δ: 2.33 (6H, s), 2.63 (2H, s), 7.17 (3H, m), 7.42 (2H, dd), 8.59 (1H, s), 8.72 (2H, dx2).

IR spectrum $\nu_{max}^{DBr}$(cm$^{-1}$): 3350, 1680, 1590.

EXAMPLE 11

1-[4-methyl-5-(4-pyridinyl)-thiazolyl-2-carbonyl]-piperidine

Piperidine (1.4 ml) was added to a stirred suspension of 4-methyl-5-(4-pyridinyl)-thiazole-2-carbonylchloride hydrochloride (400 mg) in dry toluene (4 ml) at room temperature, and the mixture was stirred at room temperature for overnight. The mixture was treated in the same manner as described in Example 6, and was recrystallized from ethyl acetate-n-hexane to give 1-[4-methyl-5-(4-pyridinyl)-thiazolyl-2-carbonyl]-piperidine (100 mg, yield 24%) as pale yellow granules.

Melting point: 139°–142° C. (decomposition).

Elementary analysis values as: $C_{15}H_{17}N_3OS$; Calculated: C=62.68, H=5.96, N=14.62 (%). Found: C=62.77, H=6.01, N=14.09 (%).

NMR spectrum (CDCl$_3$, TMS) δ: 1.70 (6H, m), 2.58 (3H, s), 3.75 (2H, m), 4.25 (2H, m), 7.40 (2H, dd), 8.70 (2H, dx2).

IR spectrum $\nu_{max}^{KBr}$(cm$^{-1}$): 1610, 1590.

EXAMPLE 12

2-cyano-4-methyl-5-(4-pyridinyl)-thiazole p-Toluenesulfonyl chloride (860 mg) was added to a stirred suspension of 4-methyl-5-(4-pyridinyl)-thiazole-2-carboxamide (450 mg) in dry pyridine (5 ml) under ice-cooling, and the mixture was stirred at 90° C. for 21 hours. The mixture was evaporated to dryness, and the residue was dissolved 2N hydrochloric acid aqueous solution (10–15 ml), washed twice with chloroform, and made alkaline by addition of 2N sodium hydroxide aqueous solution. The resulting precipitates were extracted with chloroform, washed with water, dried over magnesium sulfate, and evaporated to dryness. The residue was washed with petroleum ether, and was recrystallized from iso-propanol (twice) to give 2-cyano-4-methyl-5-(4-pyridinyl)-thiazole (220 mg, yield 53%) as pale yellow needles.

Melting point: 169°–170° C.

Elementary analysis values as: $C_{10}H_7N_3S$; Calculated: C=59.67, H=3.50, N=20.88 (%). Found: C=59.36, H=3.44, N=20.45 (%).

NMR spectrum (CDCl$_3$, TMS) δ: 2.63 (3H, s), 7.39 (2H, dd), 8.76 (2H, dx2).

IR spectrum $\nu_{max}^{KBr}$(cm$^{-1}$): 2240, 1600.

EXAMPLE 13

Methyl 4-methyl-5-(2-thiazolyl)-thiazole-2-carboxylate (i) Preparation of intermediate, 2-methoxy-5-methyl-2H-1,4-thiazin-3(4H)-one m-Chloroperbenzoic acid (28.8 g) was added dropwise to a stirred solution of 5-methyl-2H-1,4-thiazin-3(4H)-one (15 g) in methanol (300 ml) under ice-cooling and the mixture was stirred at room temperature for 1 day. After the mixture was evaporated to dryness, the residue was extracted with ethyl acetate, washed with saturated sodium bicarbonate aqueous solution and dried over anhydrous magnesium sulfate. The solvent was evaporated to dryness to give 2-methoxy-5-methyl-2H-1,4-thiazin-3(4H)-one (11.3 g, yield 61%) as pale yellow powder.

Melting point: 157°–160° C.

(ii) Preparation of intermediate, 2,2-Dimethoxy-5-methyl-2H-1,4-thiazin-3(4H)-one m-Chloroperbenzoic acid (25.6 g) was added dropwise to a stirred solution of 2-methoxy-5-methyl-2H-1,4-thiazin-3(4H)-one (16 g) in methanol (500 ml) under ice-cooling and the mixture was stirred at room temperature for 4 hours. Then, the reaction mixture was made alkaline by addition of anhydrous potassium carbonate and evaporated to dryness. The residue was extracted twice with chloroform and the combined extracts were washed with water, dried over anhydrous magnesium sulfate and evaporated to dryness. The residue was triturated with ethyl ether to give 2,2-dimethoxy-5-methyl-2H-1,4-thiazin-3(4H)-one (10 g, yield 53%) as pale yellow plates.

Melting point: 86°–88° C.

(iii) Preparation of intermediate, 2,2-dimethoxy-5-methyl-6-(3-ethoxycarbonyl-2,3-dihydro-2-thiazolyl)-2H-1,4-thiazin-3(4H)-one Ethyl chloroformate (1.0 g) was added dropwise to a stirred solution of thiazole (0.79 g) in dichloromethane (10 ml) under ice-cooling and the mixture was stirred at room temperature for 0.5 hour. Then, 2,2-dimethoxy-5-methyl-2H-1,4-thiazin-3(4H)-one (1.47 g) was added, and the mixture was stirred at room temperature for 3 hours. The solution was washed with saturated sodium bicarbonate aqueous solution, dried over magnesium sulfate and evaporated to dryness. The residue was chromatographed on silica gel (Merck Lobar column size B: Art.10401, solvent: ethyl acetate-n-hexane=2:3) to give 2,2-dimethoxy-5-methyl-6-(3-ethoxycarbonyl-2,3-dihydro-2-thiazolyl)-2H-1,4-thiazin-(4H-one (510 mg, yield 19%) as colorless prisms.

Melting point: 148°–149° C.

(iv) Preparation of intermediate, 2,2-dimethoxy-5-methyl-6-(2-thiazolyl)-2H-1,4-thiazine-3-one DDQ (206.4 mg) was added dropwise to a stirred solution of 2,2-dimethoxy-5-methyl-6-(3-ethoxycarbonyl-2,3-dihydro-2-thiazolyl)-2H-1,4-thiazine-3(4H)-one (300 mg) in dichloromethane (5 ml) at room temperature, and the mixture was stirred at room temperature for 1 hour. Then, the insoluble materials were filtered off and the solvent was evaporated to dryness.

The residue was chromatographed on silica gel (Merck Lobar column size B: Art.10401, solvent: ethyl acetate-n-hexane=2:3) to give 2,2-dimethoxy-5-methyl-6-(2-thiazolyl)-2H-1,4-thiazin-3-(4H)-one (144 mg, yield 61%) as colorless column.

Melting point: 127°–128° C.

(v) Methyl 4-methyl-5-(2-thiazolyl)-thiazole-2-carboxylate

A mixture of 2,2-dimethoxy-5-methyl-6-(2-thiazolyl)-2H-1,4-thiazin-3-(4H)-one (80 mg) and 2N hydrochloric acid solution (2 ml) was stirred at room temperature for 6 hours. Then the mixture was neutralized with saturated sodium bicarbonated aqueous solution and the resulting precipitates were collected to give methyl 4-methyl-5-(2-thiazolyl)-thiazole-2-carboxylate (58 mg, yield 82.2%) as colorless powder.

Melting point: 129°–129.5° C.

As is apparent from the foregoing description, the thiazole derivative of the present invention is a compound not described in any literature, the contractile force of isolated left atrium was significantly increased by administration of the thiazole derivative of the present invention, and the acute toxicity of the thiazole derivative of the present invention is low. Accordingly, the thiazole derivative of the present invention is effective in curing and preventing heart diseases, especially cardiac insufficiency.

As for the process of the present invention, it is advantageous from the industrial view point since the thiazole derivative of the present invention can be prepared from relatively easily available starting compounds in high yield by a relatively easy operation.

While the preferred form of the present invention has been described, it is to be understood that modifications will be apparent to those skilled in the art without departing from the true spirit of the invention. The scope of the invention, therefore, is to be determined solely by the following claims.

What is claimed is:

1. A thiazole derivative represented by the following formula I and pharmaceutically acceptable acid addition salt thereof:

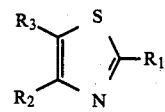

wherein $R_1$ represents —COOR$_4$,

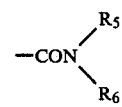

or cyano wherein $R_4$ represents hydrogen or lower alkyl, and $R_5$ and $R_6$ may be same or different and represent hydrogen, lower alkyl, aryl, amino-lower alkyl, N-lower alkylamino-lower alkyl or N,N-di-lower alkylamino-lower alkyl;

$R_2$ represents hydrogen or lower alkyl; and $R_3$ is 4-pyridinyl, 3-methyl-4-pyridinyl, 3-cyano-4-pyridinyl, 4-quinolinyl or 2-thiazolyl.

2. A compound of claim 1, wherein $R_1$ is carboxy, methoxycarbonyl, carbamoyl, methylaminocarbonyl, phenylaminocarbonyl, diethylaminocarbonyl or cyano.

3. A compound of claim 1, wherein $R_2$ is methyl.

4. 4-Methyl-5-(4-pyridinyl)-thiazole-2-carboxylic acid, according to claim 1.

5. Methyl 4-methyl-5-(4-pyridinyl)-thiazole-2-carboxylate, according to claim 1.

6. Methyl 4-methyl-5-(3-methyl-4-pyridinyl)-thiazole-2-carboxylate, according to claim 1.

7. Methyl 4-methyl-5-(3-cyano-4-pyridinyl)-thiazole-2-carboxylate, according to claim 1.

8. Methyl 4-methyl-5-(4-quinolinyl)-thiazole-2-carboxylate, according to claim 1.

9. 4-Methyl-5-(4-pyridinyl)-thiazole-2-carboxamide, according to claim 1.

10. N,4-Dimethyl-5-(4-pyridinyl)-thiazole-2-carboxamide, according to claim 1.

11. 4-Methyl-5-(4-pyridinyl)-thiazole-2-carboxanilide, according to claim 1.

12. 4-Methyl-N-(2-dimethylaminoethyl)-5-(4-pyridinyl)-thiazole-2-carboxamide, according to claim 1.

13. N,N-Diethyl-4-methyl-5-(4-pyridinyl)-thiazole-2-carboxamide, according to claim 1.

14. 2',6'-Dimethyl-4-methyl-5-(4-pyridinyl)-thiazole-2-carboxamide, according to claim 1.

15. 2-Cyano-4-methyl-5-(4-pyridinyl)-thiazole, according to claim 1.

16. A cardiotonic agent comprising a pharmaceutically acceptable excipient and, as an active component thereof, an effective amount of thiazole derivative having the following formula I:

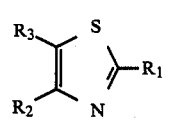

wherein $R_1$ represents —COOR$_4$,

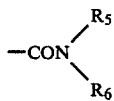

or cyano wherein
R4 represents hydrogen or lower alkyl, and
R5 and R6 may be same or different and represent hydrogen, lower alkyl, aryl, amino-lower alkyl, N-lower alkylamino-lower alkyl or N,N-di-lower alkylamino-lower alkyl;
R2 represents hydrogen or lower alkyl; and
R3 is 4-pyridinyl, 3-methyl-4-pyridinyl, 3-cyano-4-pyridinyl, 4-quinolinyl or 2-thiazolyl.

17. An agent according to claim 16, wherein the active component is 4-methyl-5-(4-pyridinyl)-thiazole-2-carboxylic acid.

18. An agent according to claim 16, wherein the active component is methyl 4-methyl-5-(4-pyridinyl)-thiazole-2-carboxylate.

19. An agent according to claim 16, wherein the active component is methyl 4-methyl-5-(3-methyl-4-pyridinyl)-thiazole-2-carboxylate.

20. An agent according to claim 16, wherein the active component is methyl 4-methyl-5-(3-cyano-4-pyridinyl)-thiazole-2-carboxylate.

21. An agent according to claim 16, wherein the active component is 4-methyl-5-(4-pyridinyl)-thiazole-2-carboxamide.

22. An agent according to claim 16, wherein the active component is N,4-dimethyl-5-(4-pyridinyl)-thiazole-2-carboxamide.

23. An agent according to claim 16, wherein the active component is 4-methyl-5-(4-pyridinyl)-thiazole-2-carboxanilide.

24. An agent according to claim 16, wherein the active component is 4-methyl-N-(2-dimethylaminoethyl)-5-(4-pyridinyl)-thiazole-2-carboxamide.

25. An agent according to claim 16, wherein the active component is N,N-diethyl-4-methyl-5-(4-pyridinyl)-thiazole-2-carboxamide.

26. An agent according to claim 16, wherein the active component is 2',6'-dimethyl-4-methyl-4-methyl-5-(4-pyridinyl)-thiazole-2-carboxamide.

27. An agent according to claim 16, wherein the active component is 2-cyano-4-methyl-5-(4-pyridinyl)-thiazole.

28. An agent according to claim 16, wherein the active component is methyl 4-methyl-5-(2-thiazolyl)-thiazole-2-carboxylate.

* * * * *